(12) United States Patent
Fisher et al.

(10) Patent No.: US 7,674,253 B2
(45) Date of Patent: Mar. 9, 2010

(54) CATHETER FOR CONDUCTING A PROCEDURE WITHIN A LUMEN, DUCT OR ORGAN OF A LIVING BEING

(75) Inventors: William T. Fisher, Schwenksville, PA (US); David E. Yaeger, Ivyland, PA (US); John E. Nash, Chester Springs, PA (US); Douglas G. Evans, Downingtown, PA (US)

(73) Assignee: Kensey Nash Corporation, Exton, PA (US)

( * ) Notice: Subject to any disclaimer, the term of this patent is extended or adjusted under 35 U.S.C. 154(b) by 338 days.

(21) Appl. No.: 11/465,767

(22) Filed: Aug. 18, 2006

(65) Prior Publication Data
US 2008/0097298 A1    Apr. 24, 2008

(51) Int. Cl.
*A61M 25/00* (2006.01)
(52) U.S. Cl. ...................................................... 604/528
(58) Field of Classification Search .......... 604/523–528
See application file for complete search history.

(56) References Cited

U.S. PATENT DOCUMENTS

| 4,723,936 | A | 2/1988 | Buchbinder et al. |
| 4,747,821 | A | 5/1988 | Kensey et al. |
| 4,926,858 | A | 5/1990 | Gifford, III et al. |
| 5,321,501 | A | 6/1994 | Swanson et al. |
| 5,383,467 | A | 1/1995 | Auer et al. |
| 5,439,000 | A | 8/1995 | Gunderson et al. |
| 5,582,171 | A | 12/1996 | Chornenky et al. |
| 5,951,482 | A | 9/1999 | Winston et al. |
| 6,001,112 | A | 12/1999 | Taylor |
| 6,134,003 | A | 10/2000 | Tearney et al. |
| 6,485,413 | B1 | 11/2002 | Boppart et al. |
| 6,585,717 | B1 | 7/2003 | Wittenberger et al. |
| 6,716,207 | B2 | 4/2004 | Farnholtz |
| 6,746,422 | B1 | 6/2004 | Noriega et al. |
| 6,842,639 | B1 | 1/2005 | Winston et al. |
| 6,852,109 | B2 | 2/2005 | Winston et al. |
| 2002/0010483 | A1 | 1/2002 | Follmer |
| 2002/0082584 | A1 | 6/2002 | Rosenman et al. |
| 2002/0198550 | A1 | 12/2002 | Nash et al. |

(Continued)

FOREIGN PATENT DOCUMENTS

JP    03209041    9/1991

(Continued)

*Primary Examiner*—Nicholas D Lucchesi
*Assistant Examiner*—Victoria P Campbell
(74) *Attorney, Agent, or Firm*—Jeffrey R. Ramberg

(57) ABSTRACT

In an embodiment, the invention provides a catheter suitable for use in performing a procedure within a vessel, lumen or organ of a living having a distal end which is steerable, such as upon the application of compression. The catheter may be of the over the wire type, or alternatively may be a rapid exchange catheter. The catheter may provide for a rotating element which may be used to open a clogged vessel, or alternatively to provide information about adjacent tissues, such as may be generated by imaging or guiding arrangements using tissue detection systems known in the art, e.g., ultrasound, optical coherence reflectometry, etc. For rapid exchange catheters having a rotating element, there is provided an offset drive assembly to allow the rotary force to be directed from alongside the guidewire to a location coaxial to and over the guidewire.

20 Claims, 13 Drawing Sheets

U.S. PATENT DOCUMENTS

2005/0240146 A1 10/2005 Nash et al.
2005/0272976 A1* 12/2005 Tanaka et al. ............... 600/114

FOREIGN PATENT DOCUMENTS

| WO | WO-99/15070 | 4/1999 |
| WO | WO-03/004086 | 1/2003 |
| WO | WO-2005/081202 | 9/2005 |

* cited by examiner

US 7,674,253 B2

CATHETER FOR CONDUCTING A PROCEDURE WITHIN A LUMEN, DUCT OR ORGAN OF A LIVING BEING

BACKGROUND OF THE INVENTION

The invention generally relates to guide catheters, specifically relating to guide catheters having a rotating working element at the distal end. The invention more particularly concerns a guide catheter capable of being used in conjunction with a guidewire, where the catheter provides a rotating working element at the distal end, such as may be used for traversing totally occluded vessels.

In the field of interventional cardiology there is a need for a percutaneously introduced intravascular device that can open totally occluded vessels. Many patients are found at diagnosis to have one or more totally occluded coronary vessels, and in the lower limbs there are even more aggressively closed vessels. Currently the options for solving these problems are as follows: A) attempt to traverse the blockage using guidewires and then follow up by dilatation and the placement of a stent: B) use a blunt dissection device like that manufactured by Cordis under the trade name 'LUMEND' device to ease the occlusion open enough to pass a wire, along which a subsequent dilatation balloon and stent are passed: C) use an electrocautery delivery wire, like that sold under the trade name 'SAFECROSS" by Intra Luminal Therapeutics, to burn a hole through the blockage and then pass a subsequent balloon dilatation catheter with stent to open the vessel: D) if all else fails pass the patient on to surgery.

All methods A) through C) have their limitations. Method A) can be extraordinarily slow, as long as two hours. Method B) is also slow and has exhibited a high degree of perforation. Method C) works well and can deal with seriously calcified lesions but could benefit by having some additional features to reduce the procedure time. Consequently there is the need for a device that can open these occlusions relatively rapidly with little risk of perforation.

The subject of this application is a device that delivers rotary energy to an atraumatic rotating tip, such as a tissue penetrating element, which, in one embodiment, can best be described as half of an elliptical spheroid with a number of flats along its sides. These flats work rather like rotating a blunt screwdriver into a piece of soft wood with the flats gradually working the fibers of the wood apart. Based on our previously patented devices such as the Kensey catheter (e.g., U.S. Pat. No. 4,747,821), we believe that such a tip can open the vessel with a low degree of trauma.

One disadvantage to current rotary devices is the need to pass the entire rotary drive over a guidewire, known as over-the-wire systems (OTW) to permit navigation of the tortuous anatomy on the way to the blockage. Such an arrangement requires a very long guidewire (300 cm) to permit control of the wire from the proximal end when the rotary device is placed along or removed from the wire.

There is also the problem of navigation as one gets close to the blockage, because by definition the wire cannot be pushed past the blockage. These problems have made the use of rotary devices in such total occlusion applications limited to virtually straight vessel anatomy such as is found in the femoral artery. Consequently in order to make a more acceptable device one preferably would incorporate steering at the distal tip to overcome the navigation problem, and a optionally monorail wire guidance (also known as a rapid exchange system) which allows the guidewire to exit the catheter at some distance typically 10-20 cm proximal from the distal tip, to allow the use of short, more manageable guidewires.

In addition there is the need for such a device to be very small in diameter (1 mm or less) if the penetration of the occlusion is to liberate a minimum of debris and if the device is to be directed into distal coronary vessels of <2 mm diameter.

All currently known rotary devices used by the cardiologist are total length OTW devices, requiring the use of 300 cm wires in order to be placed over a guidewire or removed from the guidewire. These rotary devices are placed over the guidewire, with the guidewire passageway being centrally located or coaxial to the device, in order to ensure the rotating portion remains centered about the guidewire. In order to be employed in a rapid exchange fashion, and be capable of being placed over shorter (e.g. 150 cm) guidewire, the guidewire must exit from the revolving shaft at some point, typically about 10 cm-20 cm proximal of the distal tip. Such a requirement makes it necessary to provide for some manner of offset drive at this transition point, with the input drive shaft passing alongside the guidewire exit portion off center from the guidewire center.

It should be understood that the same problem of requiring a double length guidewire could also occur with other OTW devices such as rotary intravascular ultrasound scanners, and rotary optical scanners for optical coherence tomography. Hence the systems described in this application should be considered to be applicable to any device used within a living being that incorporates a rotary input and would benefit from a means to reduce the guidewire length.

Also, no small (3 mm diameter or less) current rotary intraluminal devices incorporate a steerable distal tip. Innovative steering concepts are required to permit the steering function to exist alongside the rotary drive shafting.

In addition there are situations when special purpose guidewires such as those marketed under the name SAFE-CROSS guidewires (mentioned elsewhere in this application) or other guidewires could benefit from passage through a firm steerable catheter tip which could provide backup or support in order to steer the guidewire into an adjacent furcation, where otherwise the soft wire would tend to buckle without the additional support provided by the steerable catheter tip.

There is also the need for a low friction steerable catheter tip to permit the passage of straight stiff guidewires into a selected branch of a furcation. The straight stiff wire is often needed to navigate and penetrate a firm blockage distal of the furcation, but the anatomy demands a guidewire with a prebent tip to allow entry into the preferred branch. Clearly these are conflicting requirements, and a steerable catheter capable of guiding the stiff wire to the desired location may be beneficially employed. It is recognized that the steerable catheter may also employ a rotating component through which the stiff wire is advanced within the steerable catheter, where the rotation will serve to minimize friction forces encountered when advancing the stiff wire through the guide catheter.

It is the intent of this invention to overcome these and other shortcomings of the prior art.

SUMMARY OF THE INVENTION

In an embodiment of the present invention, a catheter for use within a living being may be used to conduct a procedure within a lumen, duct or organ of the living being. The catheter may preferably provide for a rotation of a working element, such as a tissue-penetrating tip, or alternatively, a tip to provide imaging or guiding information about adjacent tissues. Additionally, the catheter may provide for a deflectable distal end, in order to provide a steerable catheter. The catheter may be an over-the-wire (OTW) catheter, where the guidewire extends through the catheter's length. Alternatively, the catheter may be of a rapid exchange or monorail type catheter, where only a small portion of the entire length of the catheter would be placed over the wire. For the rapid exchange catheter embodiment, there is a need to provide for a transition segment, in order to allow for the guidewire to be oriented from alongside the catheter, and transition to a position inside of the catheter, and coaxial to the rotatable element. The transition segment must provide for the transmission of rotary power from a position adjacent to the guidewire, to a position coaxial about the guidewire, using an offset drive assembly.

The offset drive assembly may be a geared device, or more preferably, a friction drive arrangement to receive power input from a driveshaft alongside the guidewire, and transmit the rotary power to an output drive shaft, such as a tubular cable extended over some portion of the guidewire. A friction drive system may rely on an input roller and an output drive roller, housed in partial bearings and maintained in contact with each other in order to provide the necessary friction to transmit a rotary force. Alternatively, the offset drive subassembly may rely on a friction drive system utilizing an epicyclic friction arrangement to transmit the rotation. In the epicyclic system, a drive shaft is operatively connected to a planet roller, which as it turns, will turn against a nipper ring and an idler in the form of another planet roller. The rotation of the planet rollers will be transmitted by friction to the sun roller, itself connected to an output drive shaft, such as a tubular cable extended over some portion of the guidewire.

An embodiment of the present device may include a deflectable distal end, which allows for the steering of the device. The deflection of the distal end may be accomplished by transmitting a force such as compression or tension through at least the length of the catheter inserted into the body. In an embodiment, the deflection is accomplished by causing the deflection of spaced coils in compression, where a portion of the coils are locally frozen in position, and the deflection occurs from a reduction of space between adjacent coils away from the frozen region. Alternatively, the deflection may occur as a series of segments having pivot points are placed in compression, whereupon the segments pivot to form a curved section of the catheter. The steering may be controlled by means of a steering thimble on the catheter that remains outside of the patient when in use, where a rotation of the steering thimble may be transmitted, whether by tensioning a pull strap, or compression through a push rod, down the length of the catheter to the deflectable portion of the catheter.

DETAILED DESCRIPTION OF PREFERRED EMBODIMENTS

Figure 1A:
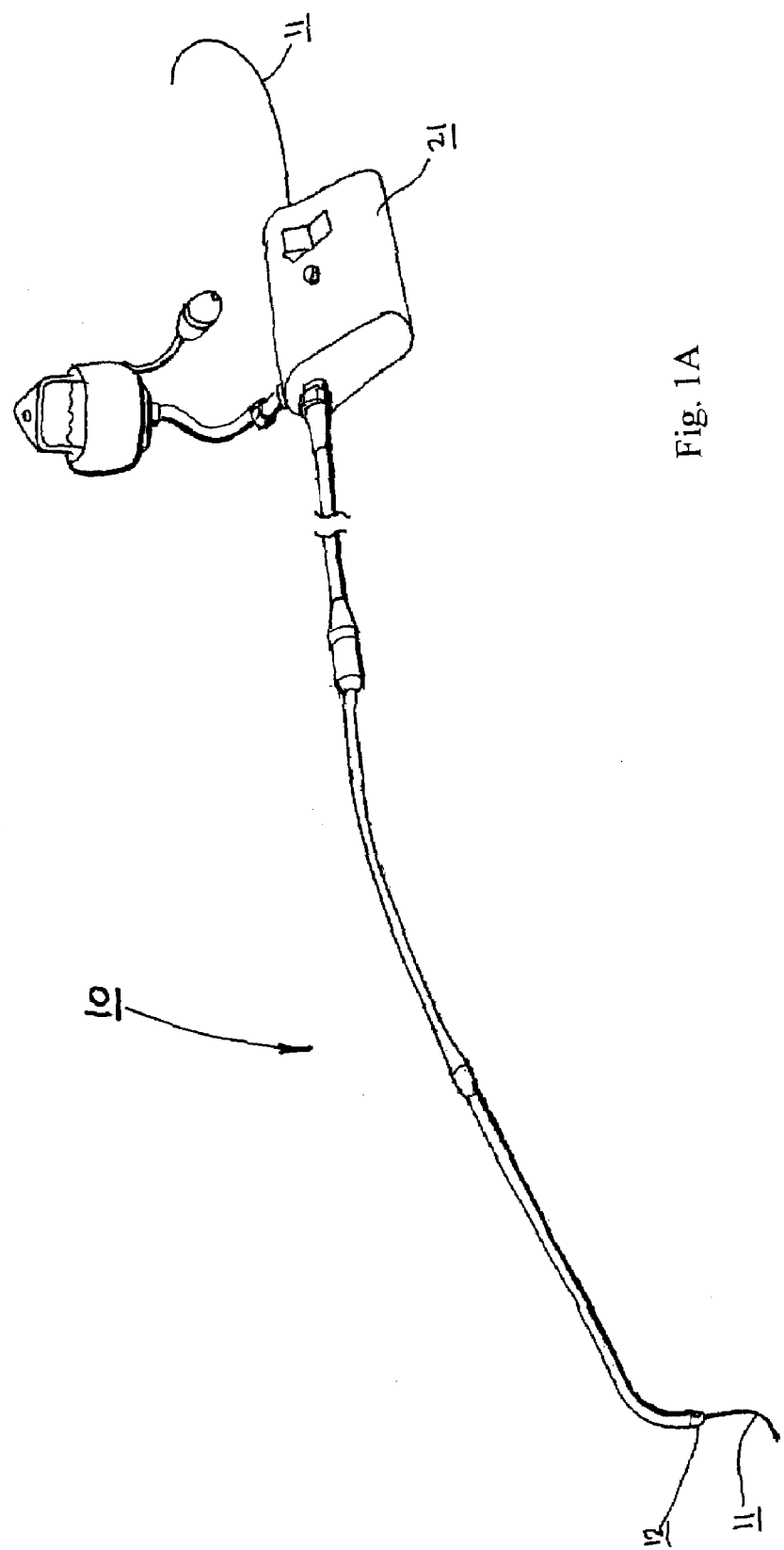
FIG. 1A is a drawing showing a schematic perception of the entire device in an over the wire configuration, typical of current technology.
Figure 1B:
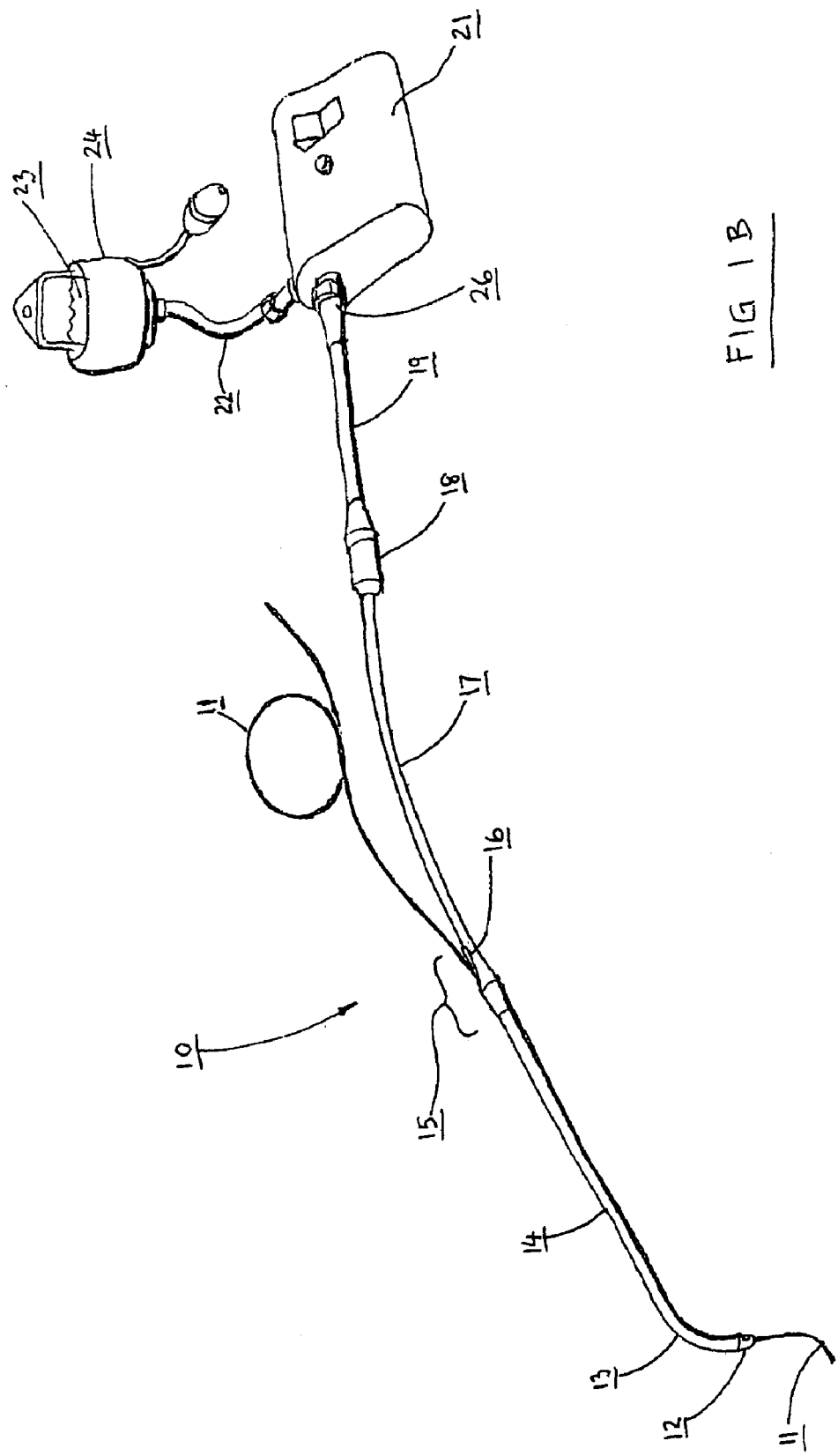
FIG. 1B is a schematic of the entire device in the preferred monorail short length over-the-wire configuration.

FIG. 1A and FIG. 1B illustrates a device (10) having a rotating working element, typically in the form of a tissue penetrating member at its distal end, shown here as rotating tip (12), suitable for opening totally occluded vessels. It is recognized that the working element may also provide other functions, such as that of a rotating scanning element, which provides detailed information via a detection system, for example through the use of ultrasound, or optical coherence reflectometry to generate information about the surrounding tissue. The difference between the devices depicted in FIG. 1A and FIG. 1B is in the manner the device slides over the guidewire (11), consequently the description provided will generally refer to FIG. 1B as the preferred arrangement of this invention, however it will be largely applicable to the device shown in FIG. 1A as well.

In FIG. 1A the device is utilized in an over the wire manner, with a guidewire that enters at the tip (12) and exits at the proximal end of the drive pack (21). This device may be preferably utilized where a guidewire exchange is desired without the need to remove the catheter device, as the guidewire may simply be removed and replaced in an over the wire arrangement. In contrast the wire in FIG. 1B enters at the tip (12) and exits at a transition segment (15). All previously known, currently available, rotary devices utilize the over the wire system of FIG. 1A, and therefore require a double length wire to allow the removal and placement of the rotary device onto the wire. In contrast, the preferred embodiment of guidewire arrangement, as illustrated by the rapid exchange device of FIG. 1B, allows the user to pass the device along a guidewire (11) in a monorail fashion where the user needs only to thread the wire through the distal segment of the device which terminates at the transition segment (15). This distance where the guidewire is threaded through such a guidewire passageway in the device is a fraction of the entire length of the device, typically of the range of 10 to 20 cm. The rest of the device is arranged to pass alongside the wire (11). With this rapid exchange catheter arrangement, the rapid exchange catheter may be placed onto or removed from a wire inserted into a patient, without requiring a double length wire, as only a short segment of the catheter is actually over the wire.

In the embodiment depicted in FIG. 1B, there is a need for an off-set drive mechanism, as there is a rotating working element arranged coaxially to guidewire (11), and the guidewire (11) is arranged to exit the distal segment (14) of the device (10) at the transition segment (15). In this embodiment, it is necessary to provide a means of transferring the drive power from a location alongside the guidewire (11), to a coaxial location, rotating around guidewire (11). It is recognized that drive power may be transmitted in any suitable form of rotary drive shaft from the drive pack (21), and then via the off-set drive mechanism, the rotary force transmission continues through drive cable (9) (as discussed later with reference to FIG. 2A), which is arranged concentrically around the guidewire (11). The offset drive mechanism is employed specifically to allow the transfer of rotary power from the side at a point within the transition segment (15). This offset drive is described more fully with relation to FIGS. 4A through 4E.

In order to make this device provide for the difficult task of opening total occlusions in tortuous narrow vessels (of the order 2-3 mm diameter) the distal portion of the device may employ a steerable distal portion (13) which can be shaped into a curve by actuation of a steering thimble (18). Cardiologists have found that if the distal portion can be shaped into a curve with a radius of say 3 mm-10 mm, such devices can be maneuvered into branch vessels if the device is torqued (twisted) and fed forward at the same time. The distal catheter body (14) is typically about 10 to 20 cm in length and of 1 mm-2 mm in diameter. In use, the cardiologist first places a guide catheter into the ostium of the appropriate coronary vessel and then maneuvers a guidewire through the guide catheter to a point as close to the total occlusion as can be reached. He then feeds the device of this invention over the wire to the same point, when the tip (12) may be just distal of the tip of the wire (11) or just proximal of the tip of the wire (11). In order to navigate the distal portions of the vessel, the user can control the deflection of the distal tip using the steerable portion (13) in concert with torsional twist applied through the proximal catheter body (17). Once the device is in place the rotary tip (12) can be actuated, and is powered by the drive pack (21) wherein power, typically electric power, for example from batteries, is supplied to a small motor (not shown) to revolve the tip (12) such that the device can then be advanced into and through the occlusion. Alternatively, the power may be supplied in form of compressed gas, which would operate a turbine motor, or other methods of generating a rotary force to be transmitted through the driveshaft. It is recognized that there might be a need to cool and lubricate the revolving tip (12), such as by supplying an irrigant (23) from a bag, optionally assisted by a pressure cuff (24). The irrigant (23) may then be directed through the device intermediate body (19) and proximal catheter body (17). This irrigant may include suitable non-thrombogenic drugs such as HEPARIN or ABCIXIMAB or PLAVIX or any other suitable drugs. Additionally, the irrigant may include saline, blood or plasma, contrast fluid, or other beneficial materials that may be introduced into a living being.

Figure 2A:
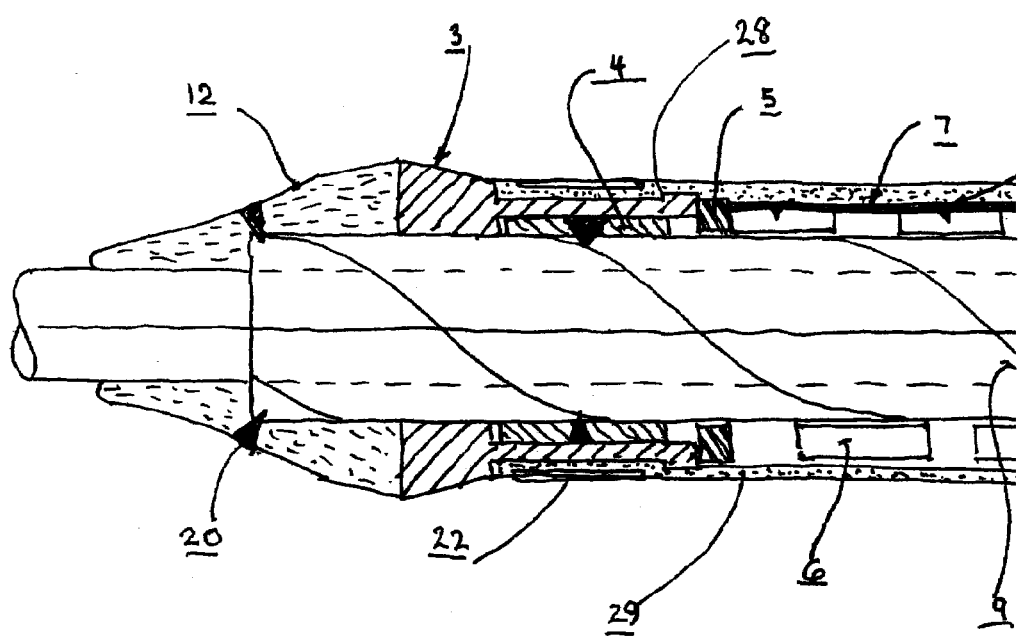
FIG. 2A is a longitudinal cross section of the distal revolving tip and drive shaft and the distal portion of one embodiment of steering mechanism.
Figure 2B:
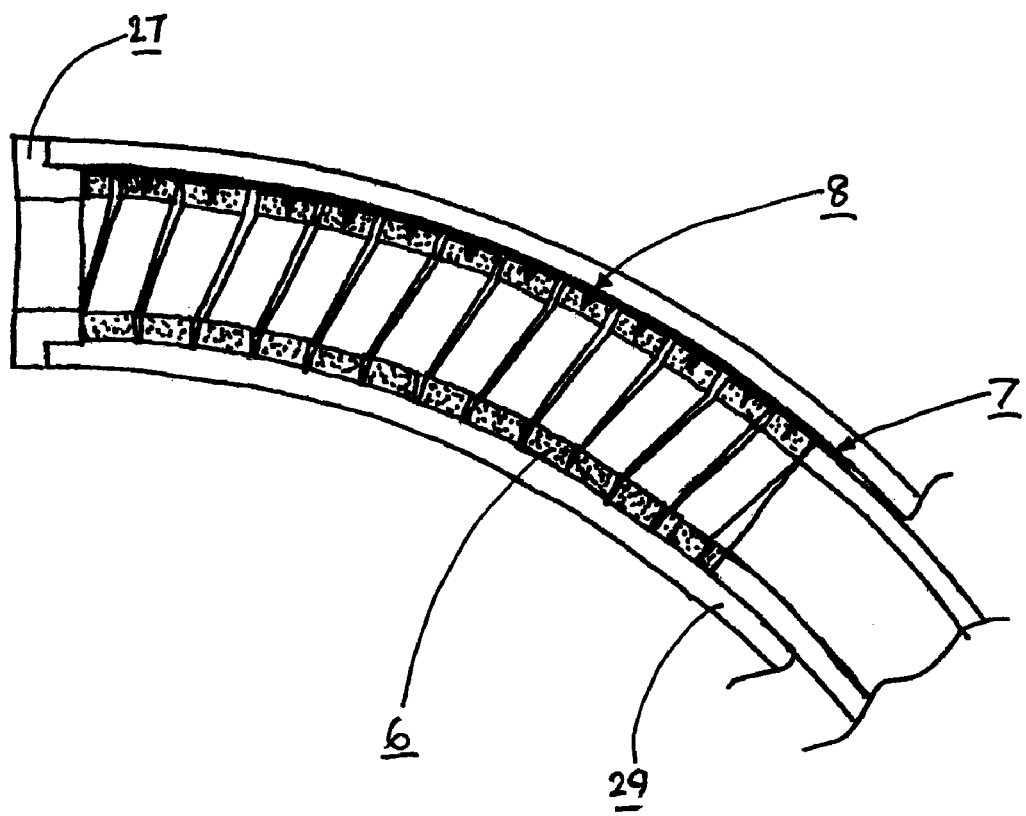
FIG. 2B is a longitudinal cross section of the steering embodiment of FIG. 2A with the tip and drive cable removed to show the action of the steering principle.

FIG. 2A shows a cross section of a typical distal portion of this invention, and one possible embodiment of a steering mechanism capable of deflecting a catheter. A multifilar hollow cable (9), capable of transmitting a torquing force and preferably fabricated from a high strength metal alloy such as 304 stainless steel or NITINOL alloy, extends along the distal body (14) and is attached to a rotating tip (12) by welds (20) or by adhesive. The tip and cable revolve in bush (3) and are located axially by a collar (4) which is welded to the cable (9). A jacket (29) encloses the assembly and is attached firmly to the bush by band (22). This jacket extends from the bush (3) to the transition segment (15) (as shown in FIG. 1B), is of 1 to 2 mm in outside diameter, and is fabricated from a flexible plastic such as PEBAX polymer, which may, or may not, incorporate braiding using metal wires or fabric filaments to enhance the torsional properties. Jacket (29) may or may not be flared to a larger diameter to contain the offset drive where it meets transition segment (15). The cable (9) runs inside a steering spring (6), preferably formed as a coil wound from flat metal ribbon, that is installed around the cable and inside the jacket (29). This spring is close wound over the proximal portion of the spring and open wound over the distal 1-2 cm of spring length. In order to accomplish the steering function, the open wound portion is in effect frozen in the open wound condition on one side of the spring and allowed to remain open on the other side: this may be accomplished by welding a strap (7) to each coil with a weld (8) over the distal portion alone. A bush (3), optionally featuring a barb (28), as shown in FIG. 2A, or bush (27) as shown in FIG. 2B, is firmly attached to the distal end of the jacket (29) to resist the application of a compressive force to the steering spring (6) from the proximal end. When this axial force is applied to this spring (6) from the proximal end, the spring (6) will transmit the force evenly over a close-coiled proximal portion but the spring will buckle into a curve at the open wound portion where the strap (7) is welded to the coils and the spring is forced to respond to the force in an asymmetric manner. FIG. 2B shows the steering spring (6) in a curved form, with the cable (9) removed, and the spring coils having been closed on the inside of the bend in response to a compressive force. Such a design provides for a minimum radius of curvature limit when the coils on the non-strap side touch as shown in FIG. 2B. It will be appreciated that open wound portions of the spring (6) could be constructed at any point in the length of the spring and that straps like that shown as item (7) could be attached on one side of the spring to locally immobilize the open wound portion. This could allow multiple portions of the catheter distal portion (13) to adopt curves in any direction and in any plane.

Figure 3A:
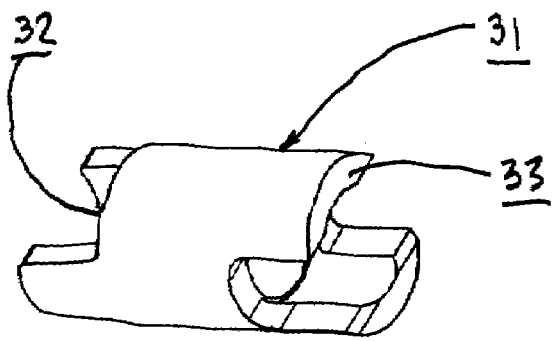
FIG. 3A is a perspective view of a single element used in another steering mechanism.
Figure 3B:
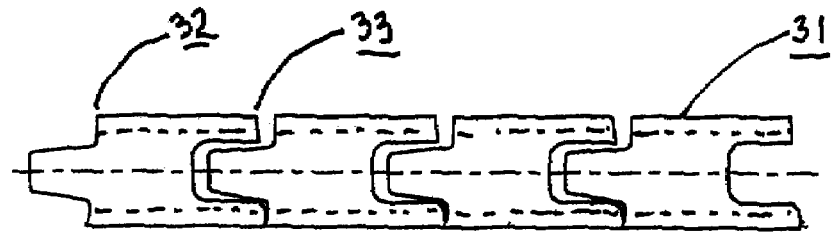
FIG. 3B shows an assembly of several of the elements of FIG. 3A in line as they become installed inside a catheter jacket.
Figure 3C:
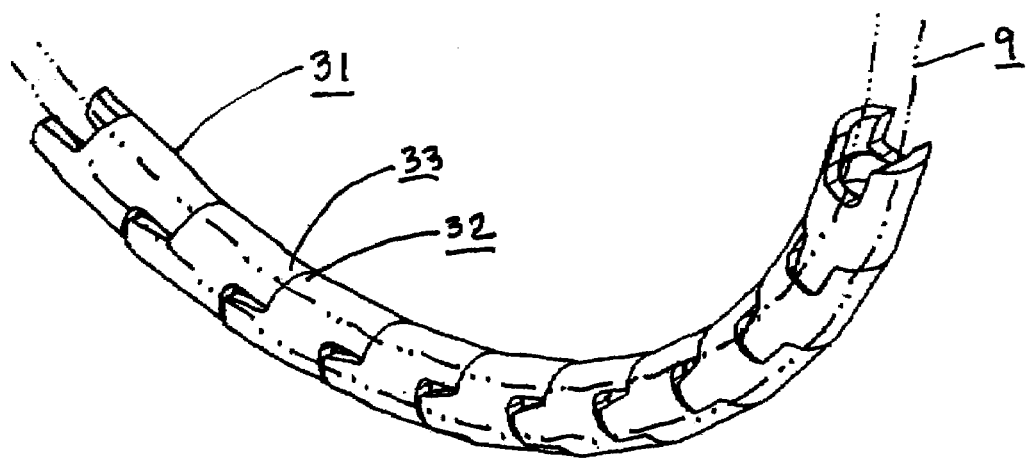
FIG. 3C is a perspective sketch of the multi element assembly of FIG. 3B formed into a curve as it would be in a catheter steerable portion.

FIGS. 3A through 3C depict an alternative form of steering mechanism that can be used in a deflectable catheter, such as the device shown in FIG. 1B. Though the steering mechanism of FIGS. 3A and 3C may be used in combination with cable (9) and rotary tip (12) as shown in FIG. 2A, the steering mechanism is quite different. In FIGS. 3A through 3C, operation of the steering is accomplished by applying a compressive load to a column (not shown) that encircles the cable (9).

This column can consist of semi flexible tube, or a close wound spring, or a stack of loose rings, which comprise the majority of the length of the distal catheter body (14). The distal 1 cm-2 cm however consists of several separate asymmetric elements (31) as shown in FIG. 3A, which are stacked in line as shown in FIG. 3B. When a compressive load is applied axially along the column the longer edges transmit the load and the shorter edges close together, thus forming the elements, and correspondingly any surrounding jacket (not shown), into a curve as shown in FIG. 3C. One advantage of this arrangement is that the edges (32) and (33) of neighboring elements (31) will close on each other as depicted in FIG. 3C and thus limit the minimum radius of curvature of the stack of elements. This limitation on minimum radius is important to provide protection for any employed spinning cable (9) (shown in phantom in FIG. 3C) by limiting the bending stress on the cable, or on any other component placed in the same central location.

Figure 5A:
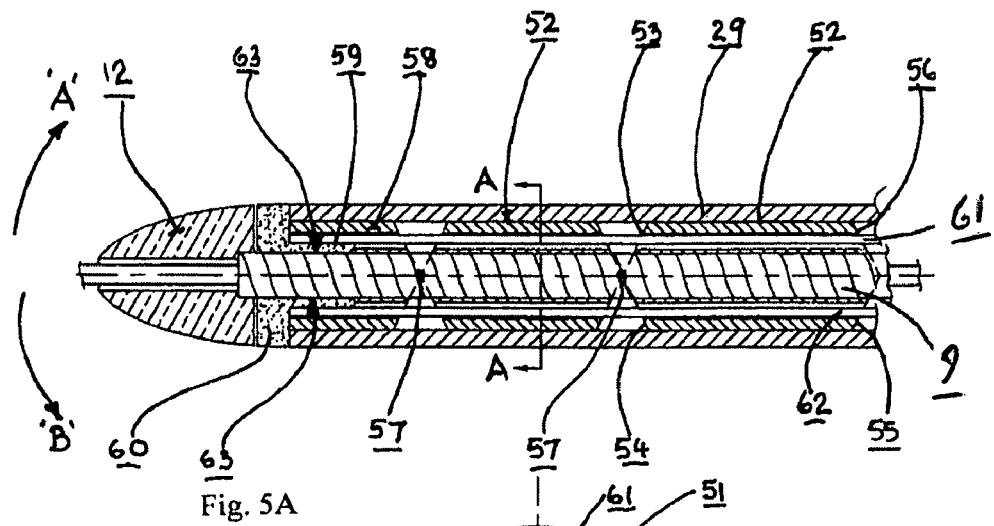
FIG. 5A is a longitudinal section of an alternative steering mechanism using segments of an extrusion and two steering straps to curve the distal tip.
Figure 5B:
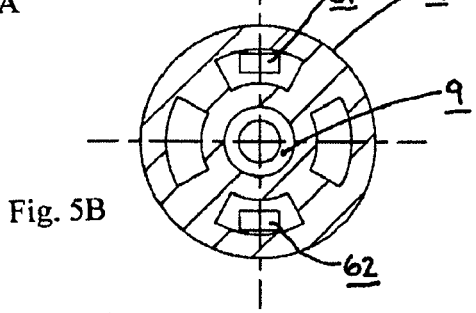
FIG. 5B is a lateral cross section through the extrusion used in FIG. 5A.
Figure 5C:
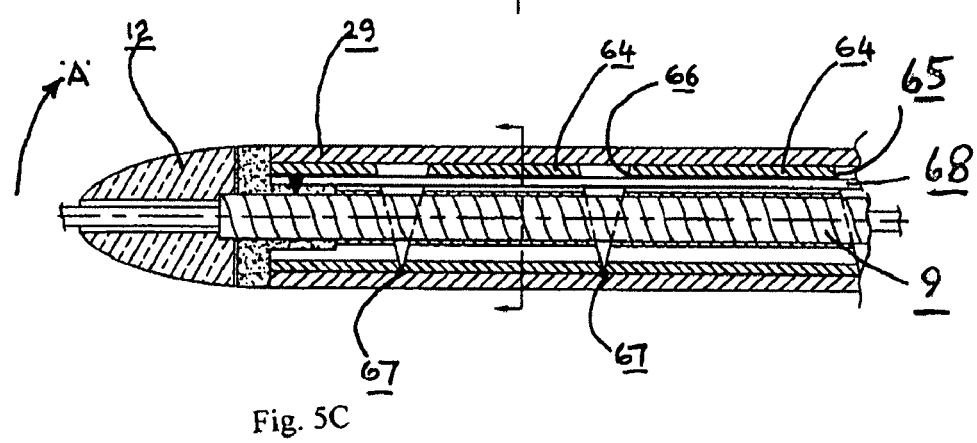
FIG. 5C is a longitudinal section of a variant of the construction shown in FIG. 5A that utilizes one steering strap.

FIGS. 5A through 5C show two alternative embodiments of steering mechanisms, which differ from those previously shown in that the steering segments are formed from an extrusion having a cross section (51) as shown in FIG. 5B. In FIG. 5A each segment (52) has flat cross cuts (53, 54, 55, 56), made at an angle away from the perpendicular to the main axis of the device. These cross cuts form ridges at which adjacent segments can pivot (57). The distal segment (58) may feature a recess (59) to accept bush (60), though the bush (60) may be affixed by other means known in the art. Cable (9) passes through the segments (52) and the bush (60) and is fastened to the tip (12) by weld or other convenient method. Steering is accomplished by tensioning or releasing straps (61) and (62), fastened to distal segment (58) by welds (63), which in turn cause the segments to pivot at contact points (57). Clearly such a design allows steering in two directions as shown by the arrows 'A' and 'B', direction 'A' being achieved by pulling on strap (61) and in direction 'B' by pulling on strap (62).

FIG. 5C is a variant of the deflectable catheter depicted in FIG. 5A and provides for steering in one direction only. In this embodiment, the segments (64), which may be formed from the extrusion (51), have only two cross cuts, (65 and 66), created at angles other than perpendicular to the main axis of the device to create pivot points (67) at the periphery. Although steering is limited to one direction 'A' in FIG. 5C when tension is applied to strap (68), the bending moment is double that of the system of FIG. 5A and can be used when that is important. In both configurations shown in FIG. 5A and FIG. 5C a catheter jacket (29) surrounds the assemblies of segments and straps.

Clearly many other forms of steering mechanism could be applied to this device, and the concepts shown above should not to be considered a limitation on the steering methods used.

Figure 8A:
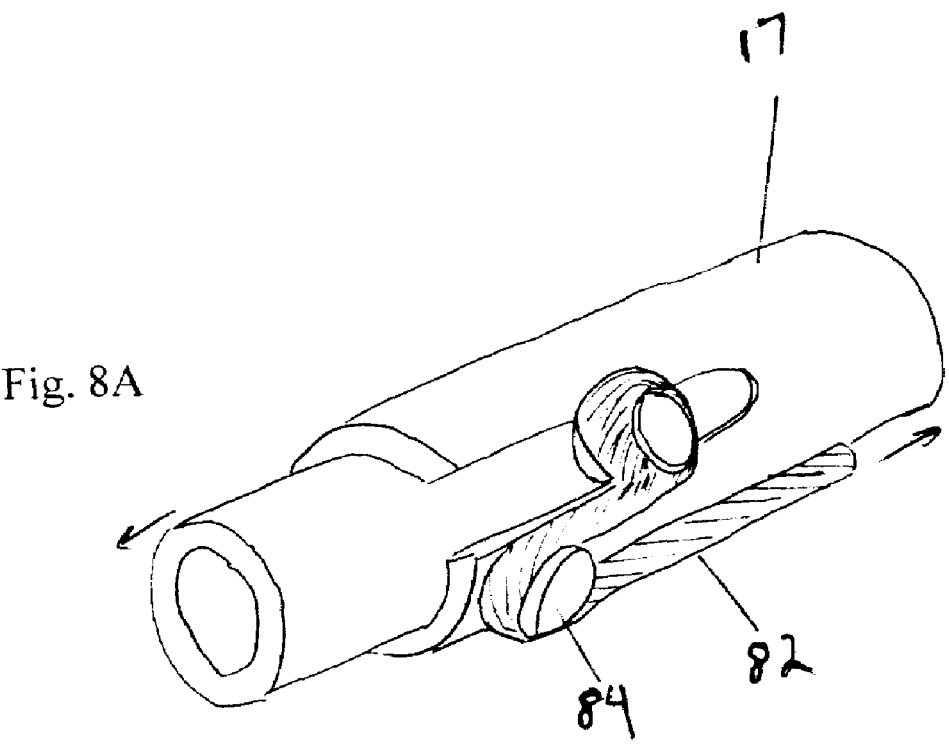
FIG. 8A is a perspective view of an embodiment of a reversing mechanism.
Figure 8B:
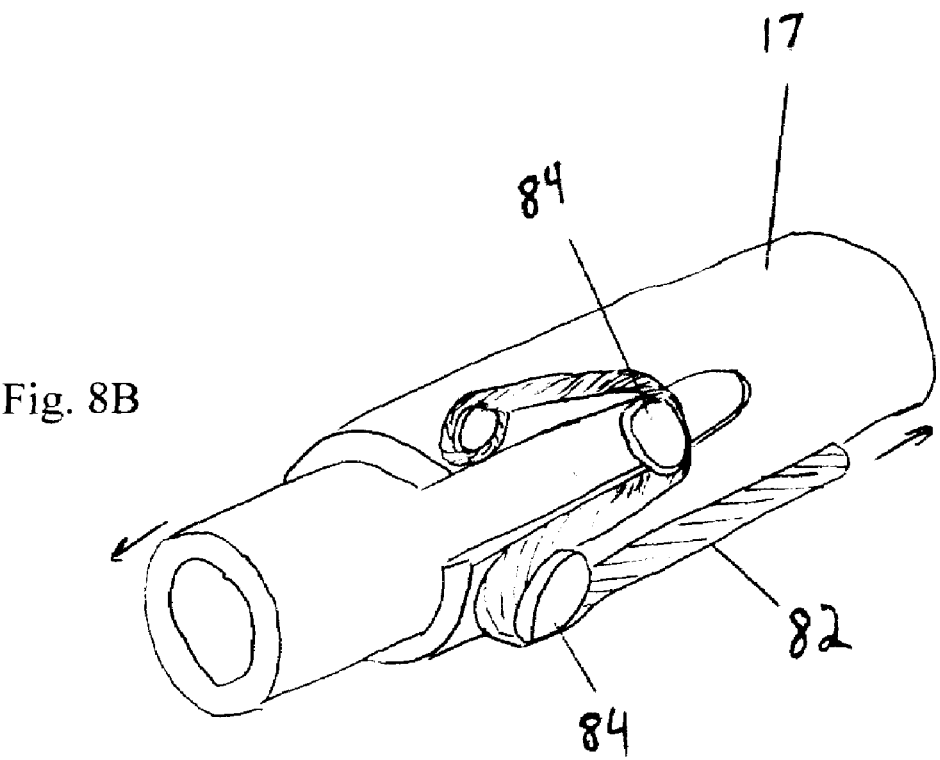
FIG. 8B is a perspective view of an embodiment of a reversing mechanism providing a mechanical advantage.

It will be appreciated from the foregoing that steering can be accomplished by tension action or compression action. It may be advantageous to use tension in the proximal catheter body (17) and compression in the distal catheter body (14). If so, a reversing mechanism, such as the embodiments shown in FIGS. 8A and 8B, is required. Such a reversing mechanism can be constructed using pulley principles, for example, using a fine cable (82) in tension passing over pegs or pulleys (84) to reverse the direction and provide compression. Such reversing by pulley action may be employed, for example, in embodiments providing a 1:1 mechanical ratio, as shown in FIG. 8A, or alternatively, mechanical advantage may be provided by doubling the wire 82 over more than one peg or pulley (84), as depicted in FIG. 8B, shown providing a 2:1 mechanical advantage.

One benefit of the steerable distal portion (13) of the device (10) of FIG. 1B with an inner rotating cable (9) (shown in detail in FIG. 2A) is the not so obvious reduction in friction as the guidewire (11) is passed through a rotating cable. Most often, the device (10) will be used in a manner where the operator feeds the device over the guidewire. But there will be times when the distal end of the guidewire is maintained proximally of the steerable portion (13) until the steerable portion has been placed in the selected branch of a furcation. The guidewire is then to be fed out from the device into the downstream lumen. However, a stiff guidewire, if employed may have a tendency to hang up and jam within the device as it tries to make the distal curve created in the device as it is steered into the selected branch, however the rotating cable (9) takes the friction vectors at right angles to the guidewire feed direction thus making it possible to navigate the curve, where a stiff wire would otherwise have not been capable of being advanced.

An embodiment of the present invention providing a rotating element at the distal end of a catheter may be useful for various surgical or interventional applications. As discussed earlier, the tip may be useful for penetrating into partially or totally occluded vessels, where the rotating action and shape of the tip may serve to separate the tissue fibers or other material forming the blockage, thereby allowing the catheter to cross the occlusion. It is recognized that, in this or other embodiments, the rotation speed may be manipulated for various applications or tissue types encountered.

Another possible use of an embodiment of the present invention is to provide information about the tissue type or location of tissue relative to the distal tip of the catheter, in order to allow diagnosis or assist in navigating the vessels or occlusion as the catheter is advanced. It is contemplated that such information could be obtained in a manner that presents a detailed image or picture (or synthesized into a picture) collected upon the rotation of the tip. This requires scanning an area for the collection of multiple contiguous streams of information, such as may be accomplished by collecting data during the rotation of the distal tip having a detection component. For example, it is known in the art to utilize a rotating element or distal tip of a catheter in order to direct energy waves, such as sound waves, or light beams, typically through a lens or prism, out in a radial or forward looking direction, to collect information about the nearby tissue as the energy wave is reflected back and detected by a detector. See for example U.S. Pat. Nos. 6,134,003; 5,383,467; 5,439,000; 5,582,171; 6,485,413; and 5,321,501. Such systems that rely on generating an image from a stream of data taken at multiple points or other scanning arrangements can be considered to be imaging systems, and may generate pictures of vessel interiors, and map locations of different tissue types and locations.

Additionally, it is recognized that a single reading, or possibly a limited number of discontinuous readings generating separate points of information could be utilized to provide guidance information about the nearby tissue, without generating a detailed image or map. For example, a single reading or very limited data collection could be utilized to generate information about the type and proximity of tissue surrounding the distal tip, allowing a decision on the safety of advancing the device (go or no go decision), or with two or more discontinuous sampling points collectively serving to indicate which particular direction which may be acceptable for advancing the device. Such limited information could be collected in a manner similar to the techniques described in U.S. Pat. Nos. 5,951,482; 6,842,639; and 6,852,109, all of which are incorporated by reference herein. While it is recognized that such a system could be incorporated into the rotating tip of the present invention, it can also be incorporated into a guidewire utilized in conjunction with the rotating tip at the distal end of the catheter. In this manner, the guidance or warning information generated by such a non-rotating central guidewire could be beneficially utilized in conjunction with a rotating distal tip to proceed through tissue blocking a vessel, without harming non-target tissue.

Transition Segment, Offset Drives

FIGS. 4A thru 4E show several different embodiments of a drive subassembly that will allow the guidewire to exit the catheter body at a point somewhere between the distal and proximal ends of the device.

Figure 4A:
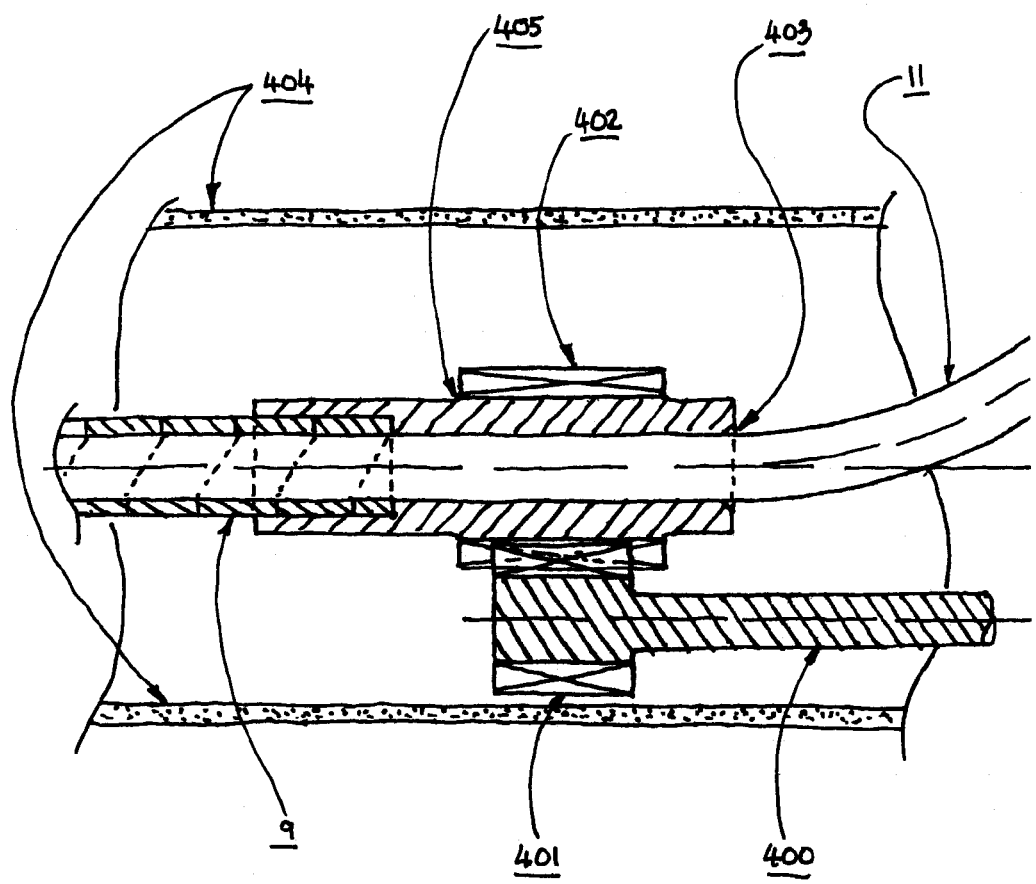
FIG. 4A is a longitudinal section of one concept, utilizing gears, for the offset drive that permits exit of the guidewire at a station somewhere along the catheter shaft.

FIG. 4A shows one possible offset drive subassembly relying on the principle of geared transmission of power, where the offset drive subassembly is arranged to allow the guidewire (11) to exit from within the cable (9) that drives the tip (not shown). In this embodiment, an input drive shaft (400) drives input gear (401) and thus output drive gear (402) which is integral with hub (405), the output gear allowing the guidewire to exit at (403). The guidewire (11) passes through the hub and thence into the cable (9) the cable being fastened to the hub by any suitable means such as weld, adhesive, or mechanical crimp. The entire offset drive assembly is housed within the outer jacket (404). Since steering is achieved by twisting of the distal body (14) via transition segment (15) and via proximal body (17), the torsional characteristics of all these components need to be symmetrical about the polar axis to ensure smooth transmission of angular position. This requirement for smooth transmission of angular position dictates that the jacket (404) be concentric with the cable (9) and guidewire (11). Such an arrangement dictates that the jacket (404) diameter is dominated by the diameter of the input gear (401) and the diameter of the output gear (402). In principle this idea is adequate, but the size of the components makes this solution impractical for a very small cardiovascular device capable of being directed into narrow vessels where the entire offset drive sub-assembly needs to reside within a transition segment of 3French to 6French total diameter (3French=1 mm), thus making the gear teeth of such a small a size that is not commercially feasible at this time.

For example if gears are used as shown in FIG. 4A, the dimensions of a typical assembly are likely to be of the order shown in Table 1. The outside diameter of the outer jacket could exceed 0.13 inch, or 10 French, well above the acceptable level of 5 French.

FIGS. 4B through 4E show two different arrangements of offset drives which transmit the drive by friction. Both of these concepts eliminate the gear tooth profiles and reduce diameter dramatically, and accordingly are capable of being utilized in narrow device applications, such as a very small cardiovascular device where the transition segment is able to be sized around 3French to 6French total diameter.

Figure 4B:
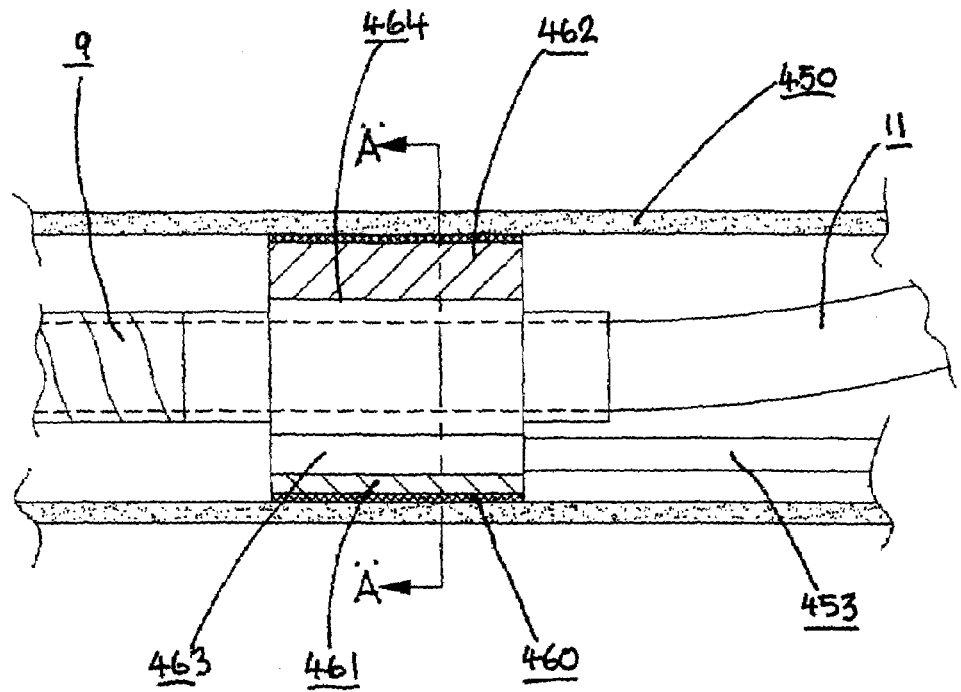
FIG. 4B is a longitudinal section of an alternative concept for the offset drive, utilizing friction drive and two rollers side by side, that permits exit of the guidewire at a station somewhere along the catheter shaft.
Figure 4C:
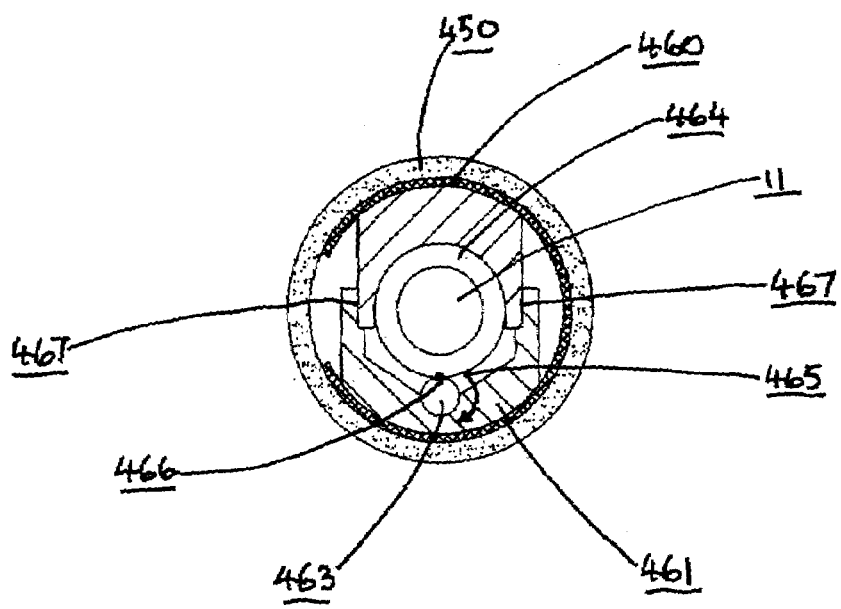
FIG. 4C is a lateral cross section of a portion of the drive shown in FIG. 4B.

FIG. 4B illustrates what could be described as a friction drive analog of the gear drive shown in FIG. 4A, with FIG. 4C showing a cross section at the line AA in FIG. 4B. In the embodiment depicted in FIGS. 4B and 4C, input drive roller (463) is pressed firmly against output drive roller (464) to permit friction drive transmission between the two rollers. The force between the rollers is applied by spring (460) through the two bearing blocks (462 and 461) to the contact point (466) between the two rollers. The guidewire (11) passes through the centerline of output drive roller (464). These two blocks can slide relative to each other in guides (467). The entire assembly is housed in outer jacket (450). Although this concept is acceptable for size, the friction losses in this system are not optimal because of the rubbing friction between the rollers (463 and 464) and their respective bearing blocks (461 and 462).

Figure 4D:
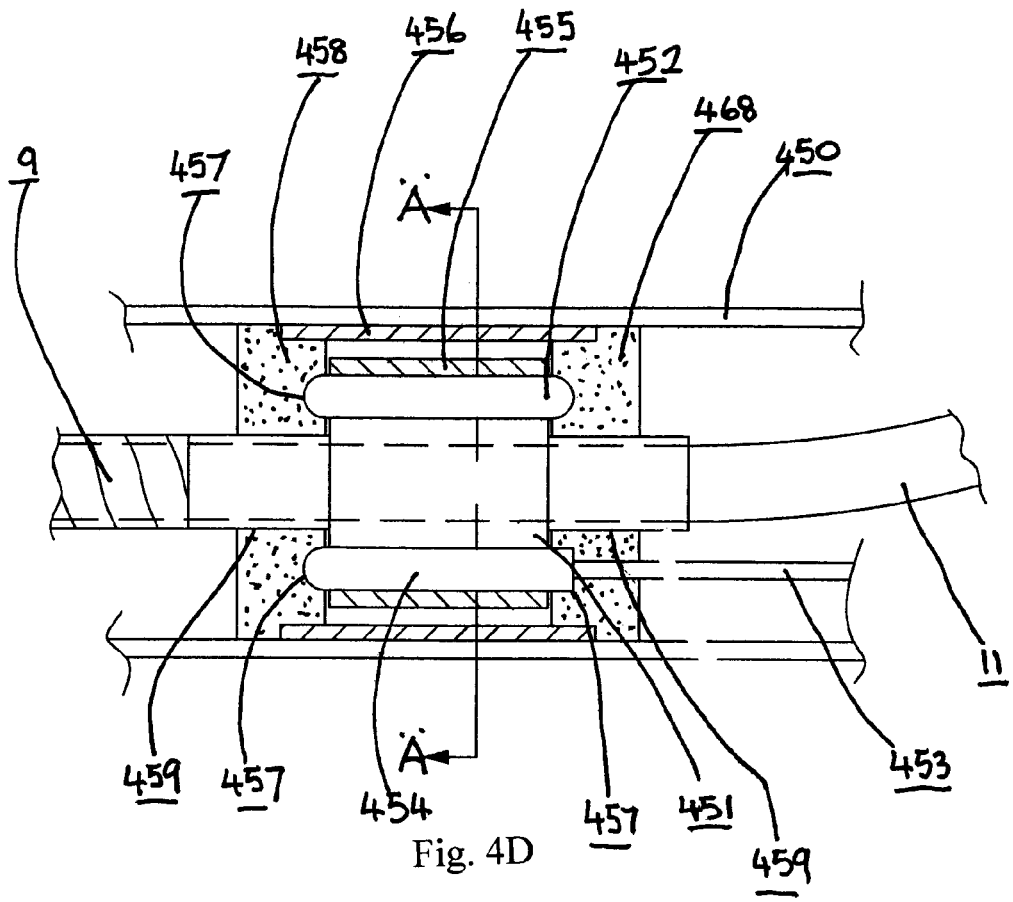
FIG. 4D shows the adoption of an epicyclic principle for yet another alternative concept for the offset drive utilizing friction drive that permits exit of the guidewire at a station somewhere along the catheter shaft.
Figure 4E:
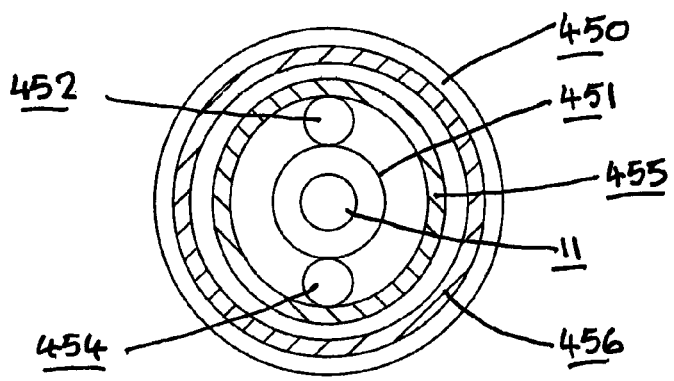
FIG. 4E is a lateral cross section of a portion of the drive shown in FIG. 4D.

An alternative embodiment of an offset friction drive subassembly is shown in FIGS. 4D) and 4E. This concept transmits drive from an input drive shaft (453) through planet (454) to sun (451) in an epicyclic fashion, with load between the rollers being supplied by nipper ring (455) and idler planet (452). Radial and axial location for the planets and sun (451) are maintained by four recesses (457) and two bores (459) provided for in the two end plates (458) and (468). The guidewire passes through the sun (451) and through the cable (9), with the joint between the sun and cable being made by any convenient method such as welding, adhesive or crimping. In order to provide radial load between the sun and planets the nipper ring is distorted with the nipper ring (455) internal diameter being less than the sum of the sun (451) diameter and the diameters of the two planets (454 and 452). The two planets (454 and 452), as well as the nipper ring (455), housed within the recesses and bores of the end plates (468 and 458) revolve as the input drive shaft (453) is turned, with the nipper ring (455) transmitting torque to the idler planet (452) which in turn transmits torque to the sun (451). In this arrangement the nipper ring (455) is rolling on the planets (452 and 454) thus reducing friction to low levels.

The entire epicyclic drive assembly is held together by housing (456) which is fastened to the two end plates (468 and 458) by any suitable means such as welding, adhesive, or crimping. This concept allows the use of very small components, for example, for components made from hardened stainless steel, a sun (451) of 0.026 inch diameter, planets (452 and 454) of 0.010 inch diameter, nipper ring (455) internal diameter of 0.043 inch, and nipper ring wall thickness of 0.003 inch. Such components allow a jacket (450) outside diameter of around 0.065 inch or 5F, much smaller than the smallest size (10.2F) currently feasible for the gear driven system of FIG. 4A and Table 1.

In order to transmit a given torque the dimensions given for the components, and therefore the load between the rollers, can be adjusted by varying the axial length of the contacts between the sun, planets and nipper ring, the axial length being of the order 0.060 inch for the diameters quoted to transmit about 0.2 in oz of torque using steel components having a coefficient of friction around 0.15.

One aspect of the difficulties of dealing with such small drives is the extremely small tolerances that are required to get an acceptable range of torque transmission. For the device described in FIG. 4C and FIG. 4D the tolerances for the planet and sun diameters need to be of the order of 50 millionths of an inch, and the wall thickness of the nipper ring needs to be held within 200 millionths of an inch if the parts are to be made from high tensile heat treated steel such as 420F. One possible way to make the manufacturing tolerances more manageable is to use materials capable of exhibiting, super-elastic, or high damping properties (e.g., NITINOL Ni—Ti Alloys, or Cu—Al—Ni alloys), for all or some of the components. By loading such super-elastic rollers (suns or planets) to a level which demands the function of the rollers in the super-elastic zone, the material strain level can be increased by more than a factor of 5:1, and the tolerances defining the nip between the nipper ring and the sun and planets can therefore be reduced.

It will be appreciated that in order to operate the steering mechanisms shown in FIGS. 2B, 3A, 3B, 3C, 5A, 5B, and 5C, there is the need to transmit force from a steering thimble (18), past or through the transition segment (15), to the distal steerable portion (13).

Figure 4F:
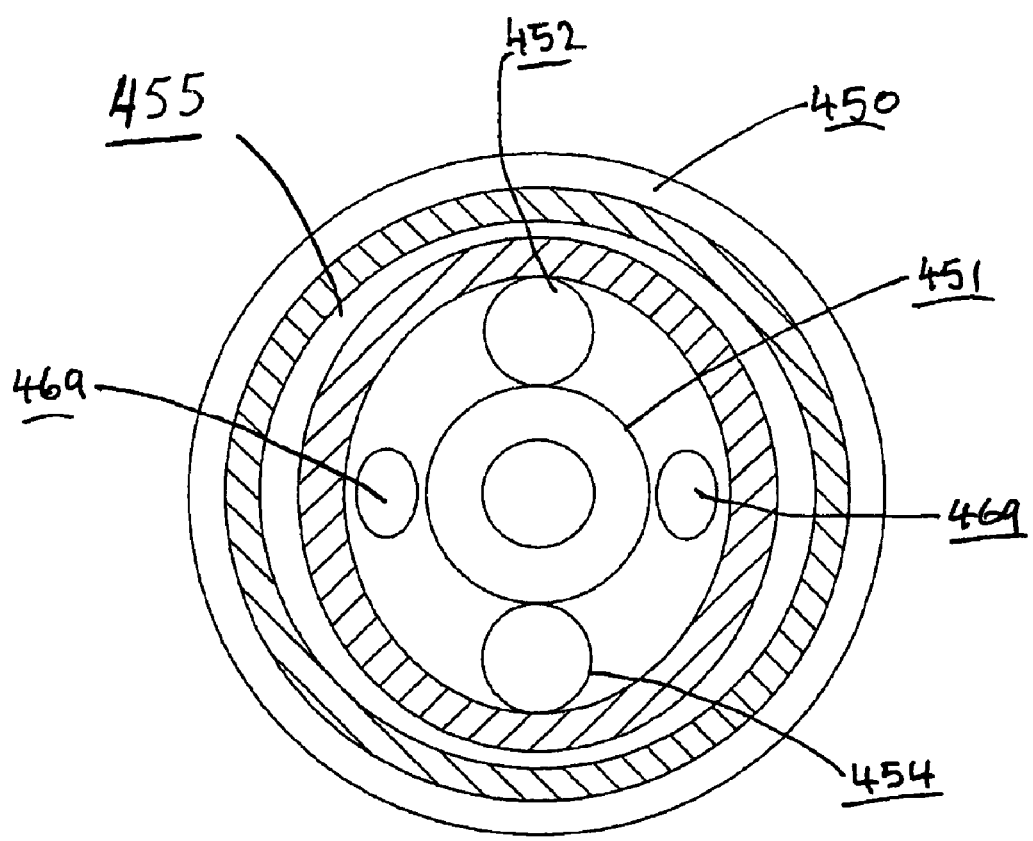
FIG. 4F is an additional lateral section through the drive of FIG. 4D showing the location for steering push rods or tension straps or wires.

This steering force can be in the form of tension via straps (61) or compression via pushrods (not shown), with the reactions taken through the outer jacket (29). One way of providing the action is by passing the straps or pushrods through the offset drive subassembly in the locations shown by numeral (469) in FIG. 4F, there being sufficient room between the nipper ring (455) and the sun (451) for straps of 0.006 thickness which can transmit loads of 10 pounds or more. Clearly this arrangement allows the transmission of tension or compression without increasing the diameter of the outer dimensions.

Transition Segment, Guidewire Exit

The transition segment (15) of device (10) in FIG. 1B is the region where the distal catheter body (14) of approximately 3F diameter changes to 5F diameter, or approximately 5F, recognizing that smaller sizes would be preferred, where the transition segment serves to accommodate an offset drive mechanism, such as any of the friction drive subassemblies described in FIGS. 4A through 4E, and provides a guidewire passageway segment that guides the guidewire from the center line of the device to a location outside the outer jacket. It is expected that, while the device 10 is in use in a patient, the distal catheter body (14) will be extended into narrow vessels approaching 2-3 mm in size, while the transition point is expected to remain in slightly larger vessels adjacent to the smaller vessels, and therefore the transition segment may be somewhat larger than the distal catheter body, typically 5F, though it is recognized that it may be somewhat larger if it is expected to remain in larger vessels or organs. The transition segment must provide for a force transmission element, such as a pushrod or alternatively a small cable and outer reaction jackets (not shown, but similar to those used in larger form for bicycle brake cables). Additionally, the transition segment must provide a space or lumen for the drive shaft to provide rotary force to the friction drive assembly, such as driveshaft (453) of FIG. 4D or FIG. 4E. In those embodiments utilizing an infusate or irrigant fluid, especially a cooling fluid, the transition segment must also provide for the passage of infusate (23). Such a component (not shown) can be made using a molded or fabricated portion made from PEBAX polymer or urethane polymers as is well known in the art, and may or may not incorporate inserts of metal, metal or synthetic braid, perforated or stamped metal, or the like, to provide for good torsional properties yet be flexible in bending.

Proximal Catheter Body

Proximal catheter body (17), shown in FIG. 1B, is typically of 4F diameter and is the final proximal portion of the device passing into the patient. This component provides a first conduit for the drive shaft (453), a second conduit for a steering mechanism such as a cable with jacket as discussed above, and additional space for infusate to flow. An extrusion of NYLON or PEBAX polymers can provide for this function and may be braided with fabric or metal filars to transmit torsion well. Alternatively this proximal body may be made from a metal tube, or from a metal tube with a multi lumen plastic insert to provide for the separation of the functions traversing this portion of the assembly. Details of this proximal catheter body are well known in the art and are not therefore shown in drawings.

Steering Thimble

Steering thimble (18), as shown in FIG. 1B, provides a control unit for actuating the steering components of the device in order to selectively deflect the deflectable portion of the device. Steering thimble (18) is preferably a small light subassembly and may provide a tensioning force to pull a cable, or alternatively a thrust to push a column, where the force generated serves to operate the distal steering function. Since this subassembly is situated integral with the proximal catheter body (17), it must be small and light so that it does not have a significant effect on the torsional characteristics of the entire catheter body (items (13 14, 15 and 17)) distal of the steering thimble. A steering thimble that is essentially circular in section and small in diameter (approximately 5-15 mm) fulfills this role. FIGS. 6 and 7 show two examples of steering thimble construction.

Figure 6A:
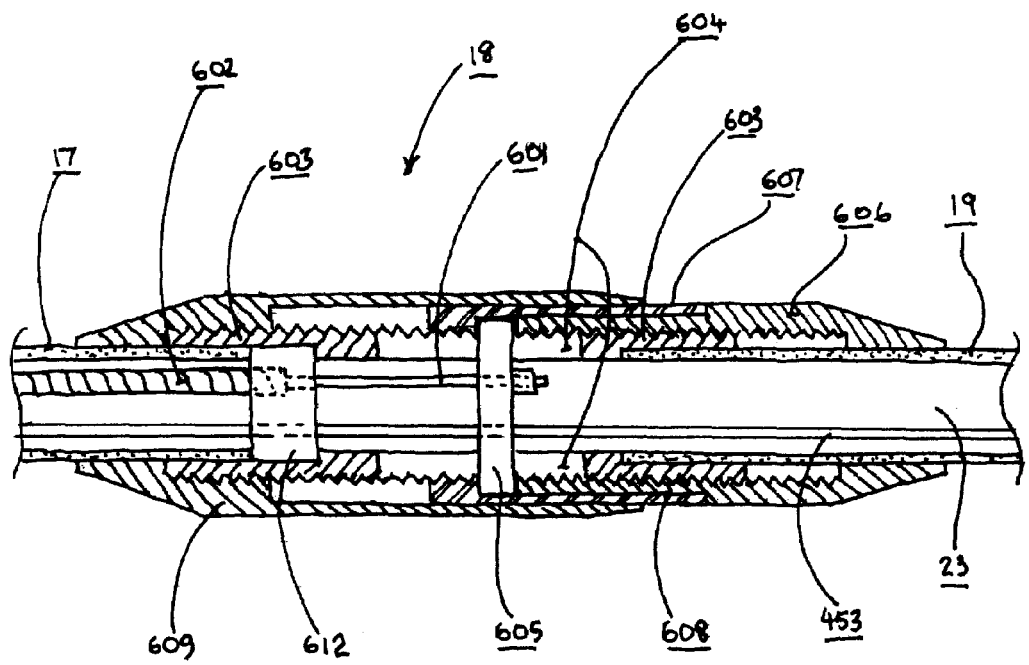
FIG. 6A is a longitudinal section one type of tension transmission device, based on typical bicycle cable brake technology, that passes from the proximal end of the device to the offset drive location.
Figure 6B:
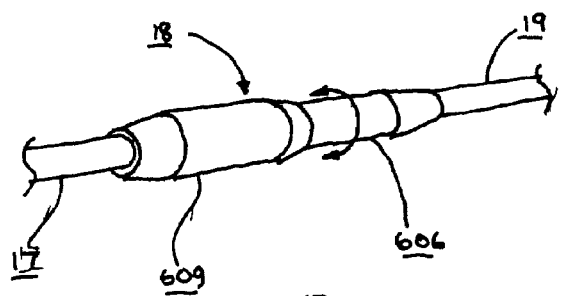
FIG. 6B is a perspective view of the steering thimble sectioned in FIG. 6A.

FIG. 6A shows an arrangement that is designed to apply tension to a cable or wire (601) that passes through outer reaction jacket (602) to operate a distal steering function, such as that shown in FIG. 5A or 5C. Steering thimble (18) anchors proximal catheter body (17) and intermediate catheter body (19) in recesses in barrel (603) using adhesives or thermal bonding. Barrel (603) can be made from polycarbonate or nylon or other light polymer, with or without fillers. Any suitable adhesives capable of joining the components are suitable for this purpose, for example UV cured adhesives or anaerobic curing, wicking adhesives, such as LOCTITE 4011 medical adhesive, may successfully be employed. In the depicted embodiment, two slots (604) are cut diametrically opposed to each other in barrel (603) for the purpose of receiving plate (605) which can slide along the axis of the thimble (18) under the action of threaded sleeve (606) and ferrule (607). Threaded sleeve (606) and ferrule (607) are both made from a light strong polymer such as polycarbonate and are bonded together at interface (608) using a suitable adhesive, such as LOCTITE 4011 medical adhesive. Cover (609) provides protection for slots (604), limits infusate (23) leakage, and provides the distal portion of the thimble which is grasped and held stationery, whilst the proximal portion (606) is twisted to apply tension to the cable (601), as shown in FIG. 6B. The cable reaction is taken through outer reaction jacket (602) which terminates at insert (612) at the proximal end and the offset drive end plate (468) of FIG. 4D at the distal end where the internal cable or wire (601) continues to pass through the offset drive as shown as item (469) in FIG. 4F and down the distal catheter body (14) to operate, for example, the pull strap (68) shown in FIG. 5C, or other tensioning steering mechanisms.

Figure 7A:
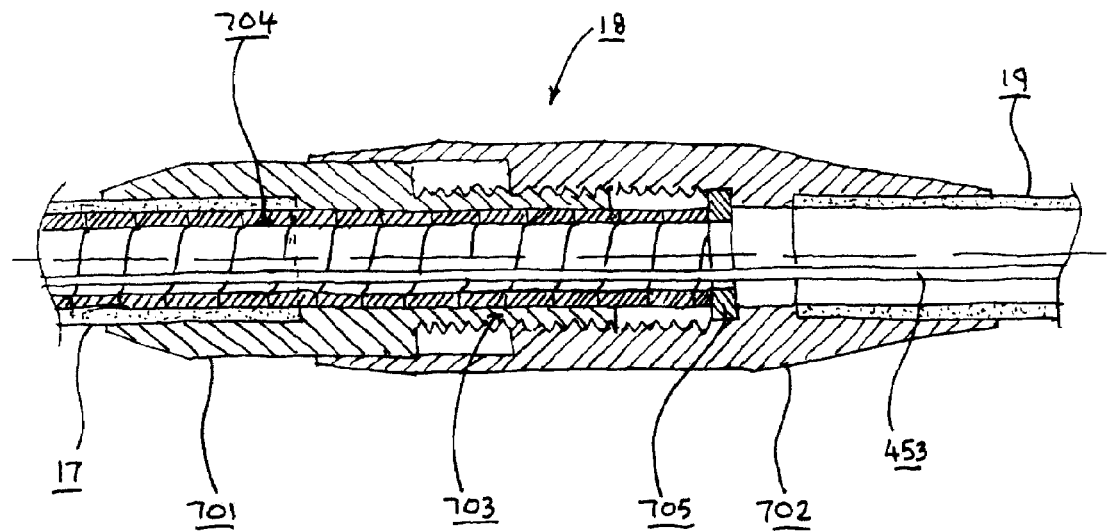
FIG. 7A is a longitudinal section of a steering thimble that applies compression to a spring or column to effect steering.
Figure 7B:
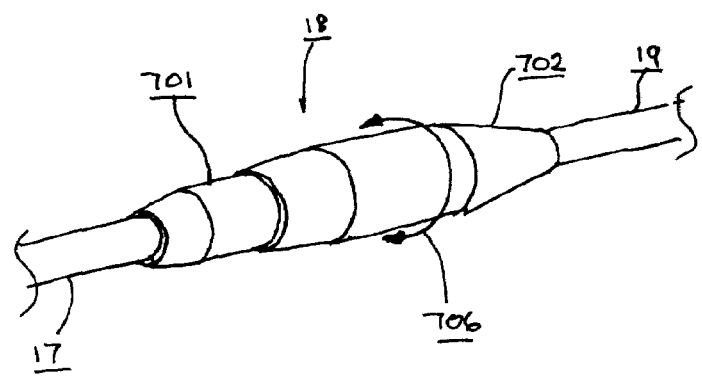
FIG. 7B is a perspective view of the steering thimble mechanism shown in FIG. 7A.

FIG. 7A is an axial section illustrating a steering thimble (18) for the operation of steering concepts using compression to drive the distal steerable portion (13) of FIG. 1B as shown, for example, in FIG. 2B. Ferrule (701) provides the termination point for proximal catheter body (17) and threaded sleeve (702) anchors the intermediate catheter body (19). Both joints are secured using any suitable adhesive, such as LOCTITE 4011 adhesive. Ferrule (701) incorporates a threaded extension (703) on which is mated threaded sleeve (702). The component under compression, spring (704) is driven by thrust washer (705) from threaded sleeve (702). As mentioned earlier, the component under compression can be a close wound spring, a piece of tubing or a stack of cylinders, all of which can transmit compression yet provide for bending flexibility of the catheter body. Ferrule (701) and threaded sleeve (702) can be made from polycarbonate, nylon, or ABS or any other strong light polymer, or other suitable materials, such as metal alloys, such as alloys of aluminum, titanium or stainless steel. Thrust washer (705) can be made from polycarbonate or other hard polymer or a metal such as stainless steel, and can be coated with an antifriction material such as TEFLON polytetrafluoroethylene. Spring (704) extends distally from steering thimble (18), through proximal catheter body (17) and via pushrods (not shown) bypasses the transition segment (15), bypasses the offset drive as indicated by items (469) on FIG. 4F, and then operates a distal steering spring such as that shown as item (6) in FIG. 2B. FIG. 7B shows an overview of the steering thimble of FIG. 7A and shows the direction of torque application by arrow (706).

In both FIG. 6A and FIG. 7A the input drive shaft (453) traverses the steering thimble assembly, such that the transmission of rotary force from the drive pack (21) to the offset drive subassembly is not affected by the operation of steering thimble (18).

It will be noted that the steering thimble of FIG. 6A has a design that keeps the proximal catheter body (17) and the intermediate catheter body (18) in rigid axial and rotational relationship, with the steering function provided by threaded sleeve (606) revolving about the barrel (603). In the design of FIG. 7A the intermediate catheter body (19) revolves when the steering is activated and the intermediate body (19) moves axially relative to proximal body (17). Clearly the designs of FIG. 6A or FIG. 7A could both incorporate either feature if so desired.

Swivel

In order for the operator to use the steering function, the catheter in-toto, distal of the steering thimble, must be capable of being rotated about its axis in order to point the steerable portion (13) in the desired direction. For this to be achieved it is necessary to incorporate a swivel somewhere in the intermediate catheter body (19) that allows the independent rotation of one portion of the catheter independently from another portion of the device and permits the operator to rotate the catheter with as little drag as possible from the drive pack. In FIG. 1B the swivel (26) is located at the drive pack (21), but it could just as well be situated at the proximal end of the steering thimble (18) or at somewhere along the intermediate catheter body. No design is shown for this feature since such swivels are well known in the art, the first being marketed in a product known as the Kensey Catheter by Cordis in the 1987 to 1992 time frame.

Drive Pack

The drive pack (21) of FIG. 1B is not shown in detail since all aspects of this drive are similar to a drive disclosed under Kensey Nash application Ser. No. 10/832,830 entitled "Thrombectomy and Soft Debris removal Device" and now approved for sale under the name "THROMCAT™ Thrombectomy Catheter System". Basically the drive pack provides rotary power from a small DC motor, power from batteries for the motor, a power on/off switch, an indicator light, and for some applications a logic board and suitable power switching functions to permit motor speed to be varied as a function of time. For example the speed might be ramped up in one direction and then reversed and ramped up in the other direction, or the speed might be varied in saw tooth or sine waves in one direction. In addition the drive pack accepts infusate via lumen (22) from a bag with cuff (24) for delivery through swivel (26) to the intermediate catheter body (19) and subsequently to the area adjacent to the rotary tip (12).

In FIG. 1B the guidewire (11) passes through the drive pack and exits the drive pack via a hemostasis valve (not shown) as is common in the art for OTW applications It is recognized that any features described in the present application may be used alone or in combination with other described features. Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A rapid exchange catheter for conducting a procedure within a lumen, duct or organ of a living being comprising:
   a working element arranged at a distal portion of said catheter, said working element having an axis of rotation;
   a guidewire passageway arranged through said working element and co-axial with said axis of rotation; and
   a drive input shaft having a rotary drive axis offset radially from said working element axis of rotation, wherein said drive input shaft is arranged to effect said rotation of said working element through an offset drive mechanism, and further wherein at least a portion of said drive input shaft is located 10-20 cm from a distal tip of said catheter.

2. The rapid exchange catheter of claim 1, arranged to fit within a Number 5 French catheter.

3. The rapid exchange catheter of claim 2, wherein at least some of the components making up the offset drive comprise materials capable of exhibiting at least one of super-elasticity and high damping.

4. The rapid exchange catheter of claim 1, wherein said offset drive mechanism comprises a friction drive system.

5. The rapid exchange catheter of claim 4, wherein said offset drive mechanism comprises an epicyclic drive assembly comprising at least two planet rollers, a nipper ring and a sun roller.

6. The rapid exchange catheter of claim 5, wherein said sun and planet rollers have a tolerance of at least about 250 millionths of an inch.

7. The rapid exchange catheter of claim 5, wherein said epicyclic drive assembly is arranged to receive power input from said drive input shaft arranged to cause the rotation of one of said planet rollers, whereupon said power is transmitted by friction in an epicyclic manner and is output from said sun roller to effect the rotation of said working element.

8. The rapid exchange catheter of claim 7, wherein said sun roller is arranged to coaxially accept the slidable passage of a guidewire therethrough.

9. The rapid exchange catheter of claim 5, wherein at least one of the nipper ring, sun roller, or planet rollers comprises an alloy having superelastic properties.

10. The rapid exchange catheter of claim 1, further comprising a drive motor and associated controls, said drive motor being arranged to effect the rotation of said drive input shaft.

11. The rapid exchange catheter of claim 10, further comprising a swivel located distally of said drive motor and associated controls, said swivel being arranged to allow the independent rotation of said rapid exchange catheter independently of said drive motor.

12. The rapid exchange catheter of claim 1 wherein the distal end is arranged to be deflected.

13. The rapid exchange catheter of claim 12, wherein said deflectable distal end comprises a coiled spring arranged to be deflected and thereby vary the shape of the distal end of the catheter.

14. The rapid exchange catheter of claim 13, wherein at least a portion of said coiled spring comprises a first side and a second side, where, on the first side, at least a portion of the coils are immobilized locally in an open coil relationship, such that upon application of a compressive load along the axis of said open coiled spring, said first side resists collapse on the immobilized side, and said second side, which is not immobilized, collapses in response to the application of a compressive load, whereupon said coiled spring assumes a curved orientation.

15. The rapid exchange catheter of claim 12, wherein said deflectable distal end is actuated by a steering thimble, arranged to be rotated to transmit a deflecting force distally through the rapid exchange catheter.

16. The rapid exchange catheter of claim 15, wherein said deflecting force is transmitted through a reversing mechanism to convert a tensile force into a compressive force.

17. The rapid exchange catheter of claim 1, wherein said rotation of said working element minimizes frictional resistance for the advancement of a guidewire through said guidewire passageway.

18. A rapid exchange catheter for conducting a procedure within a lumen, duct or organ of a living being comprising:
   a working element arranged at a distal portion of said catheter, said working element having an axis of rotation;
   a guidewire passageway arranged through said working element and co-axial with said axis of rotation; and
   a drive input shaft having a rotary drive axis offset radially from said working element axis of rotation, wherein said drive input shaft is arranged to effect said rotation of said working element through an offset drive mechanism, wherein at least said working element, said guidewire passageway and said drive input shaft are arranged to fit within a single catheter not larger than Number 10 French.

19. A rapid exchange catheter for conducting a procedure within a lumen, duct or organ of a living being comprising:
   a working element arranged at a distal portion of said catheter, said working element having an axis of rotation;
   a guidewire passageway positioned within said working element and co-axial with said axis of rotation; and
   a drive input shaft having a rotary drive axis offset radially from said working element axis of rotation, wherein said drive input shaft is arranged to effect said rotation of said working element through an offset drive mechanism, wherein at least said portion of said drive input shaft that engages said working element is located within said living being when said catheter is in use in said procedure.

20. The rapid exchange catheter of claim 19, further comprising a transition segment, and wherein said transition segment also is located within said living being during use.

* * * * *